(12) United States Patent
Eddy et al.

(10) Patent No.: US 8,538,773 B2
(45) Date of Patent: Sep. 17, 2013

(54) HEALTHCARE QUALITY MEASUREMENT

(75) Inventors: David M. Eddy, Aspen, CO (US);
Joshua Adler, Tampa, FL (US);
Macdonald Scott Morris, Atherton, CA (US)

(73) Assignee: Archimedes, Inc., San Francisco, CA (US)

( * ) Notice: Subject to any disclaimer, the term of this patent is extended or adjusted under 35 U.S.C. 154(b) by 141 days.

(21) Appl. No.: 12/788,242

(22) Filed: May 26, 2010

(65) Prior Publication Data

US 2010/0305964 A1    Dec. 2, 2010

Related U.S. Application Data

(60) Provisional application No. 61/181,636, filed on May 27, 2009, provisional application No. 61/181,663, filed on May 27, 2009.

(51) Int. Cl.
*G06Q 10/00* (2012.01)
*G06Q 50/00* (2012.01)

(52) U.S. Cl.
USPC .................................. 705/2; 705/3; 600/300

(58) Field of Classification Search
USPC .......................................... 705/2–3; 600/300
See application file for complete search history.

(56) References Cited

U.S. PATENT DOCUMENTS

| | | | |
|---|---|---|---|
| 6,108,635 A | 8/2000 | Herren et al. | |
| 6,949,342 B2 | 9/2005 | Golub et al. | |
| 6,985,846 B1 | 1/2006 | Dunlavey | |
| 7,260,480 B1 | 8/2007 | Brown et al. | |
| 2004/0152056 A1 | 8/2004 | Lamb et al. | |
| 2005/0119534 A1 | 6/2005 | Trost et al. | |
| 2005/0131663 A1 | 6/2005 | Bangs et al. | |
| 2006/0129427 A1 | 6/2006 | Wennberg | |
| 2006/0173663 A1 | 8/2006 | Langheier et al. | |
| 2007/0026365 A1 | 2/2007 | Friedrich et al. | |
| 2007/0239490 A1 | 10/2007 | Sullivan | |
| 2008/0015894 A1 | 1/2008 | Miller et al. | |
| 2008/0091471 A1 | 4/2008 | Michon et al. | |
| 2008/0147440 A1 | 6/2008 | Kil | |
| 2008/0275729 A1 | 11/2008 | Taggart et al. | |

(Continued)

FOREIGN PATENT DOCUMENTS

WO    WO 2005/117553    12/2005

OTHER PUBLICATIONS

Notification of Transmittal of the International Search Report and the Written Opinion of the International Searching Authority, or the Declaration received in PCT Application No. PCT/US09/62005 dated Jun. 14, 2010 (11 pages).

(Continued)

*Primary Examiner* — Luke Gilligan
(74) *Attorney, Agent, or Firm* — Hickman Palermo Truong Becker Bingham Wong LLP

(57) ABSTRACT

A method of determining a quality of care provided by a healthcare provider to individuals in a population is provided. A data processing apparatus that has one or more processors is disclosed. Data representing biomarkers for individuals in a population is received. Baseline and present risks are determined. Risk reduction values are determined. Based on the current risk reduction, a quality score is determined. A scale is created, and the quality score is mapped to the scale. The global quality score of the disclosure provides numerous benefits over past performance measures.

27 Claims, 8 Drawing Sheets

(56) References Cited

U.S. PATENT DOCUMENTS

| | | | |
|---|---|---|---|
| 2009/0150180 A1* | 6/2009 | Cohen et al. | 705/3 |
| 2009/0254375 A1 | 10/2009 | Martinez et al. | |
| 2010/0004945 A1* | 1/2010 | Petratos et al. | 705/2 |
| 2010/0185399 A1* | 7/2010 | Slotman | 702/19 |
| 2010/0198571 A1 | 8/2010 | Morris et al. | |
| 2010/0305964 A1 | 12/2010 | Eddy et al. | |
| 2011/0082350 A1 | 4/2011 | Koh | |
| 2011/0119212 A1 | 5/2011 | DeBruin et al. | |
| 2011/0173027 A1 | 7/2011 | Olszewski et al. | |
| 2011/0199212 A1 | 8/2011 | Matityaho et al. | |

OTHER PUBLICATIONS

Current Claims for PCT Application No. PCT/US09/62005, Jul. 2010 (7 pages).

"Notification of Transmittal of the International Search Report and the Written Opinion of the International Searching Authority, or the Declaration" received in International application No. PCT/US10/55010 dated Jul. 1, 2011, 8 pages.

Current Claims of International application No. PCT/US10/55010 dated Jul. 2011, 7 pages.

Singh, D. et al., "Gene Expression Correlates of Clinical Prostate Cancer Behavior" *Cancer Cell*, dated Mar. 2002, 7 pages.

Stephenson, R. et al., "Flow Cytometry of Prostate Cancer: Relationship of DNA Content to Survival" *American Association for Cancer Research* dated: May 1, 1987, 5 pages.

European Search Report received in Application No. 06789730.6 dated Jan. 4, 2011 (1 page).

Current claims of European Application No. 06789730.6 dated Jan. 2011 (5 pages).

Schmittdiel, J. et al., "Predicted Quality-Adjusted Life Years as a Composite Measure of the Clinical Value of Diabetes Risk Factor Control" Medical Care (Apr. 2007) pp. 315-321.

U.S. Appl. No. 12/611,785, filed Nov. 3, 2009, Final Office Action, Jun. 19, 2012.

Tannock et al. Chemotherapy with mitoxantrone plus prednisone or prednisone alone for symptomatic hormone-resistant prostate cancer. A Canadian randomized trial with palliative end points. Journal of Clinical Oncology, vol. 124, Dated 1996, 9 pages.

Received Office Action in U.S. Appl. No. 11/503,393, filed Aug. 11, 2006, mailed on Dec. 22, 2010.

Received Restriction Requirement in U.S. Appl. No. 12/476,907, filed Jun. 2, 2009, mailed on Apr. 15, 2011.

Received Final Office Action in U.S. Appl. No. 11/503,393, filed Aug. 11, 2006, mailed on May 10, 2011.

Received Office Action in U.S. Appl. No. 12/146,727, filed Jun. 26, 2008, mailed on Jun. 14, 2011.

Received Office Action in U.S. Appl. No. 12/476,907, filed Jun. 2, 2009, mailed on Jun. 21, 2011.

Received Office Action in U.S. Appl. No. 12/476,907, filed Jun. 2, 2009, mailed on Jan. 13, 2012.

Received Office Action in U.S. Appl. No. 12/611,785, filed Nov. 3, 2009, mailed on Jan. 5, 2012.

Received Notice of Allowance, in U.S. Appl. No. 12/146,727, filed Jun. 26, 2008, mailed on Jan. 20, 2012.

U.S. Appl. No. 12/476,907, filed Jun. 2, 2009, Final Office Action, May 15, 2012.

U.S. Appl. No. 11/503,393, filed Aug. 11, 2006, Examiner's Answer, Jun. 5, 2013.

* cited by examiner

HEALTHCARE QUALITY MEASUREMENT

BENEFIT CLAIM/RELATED CASES

This application claims the benefit under 35 U.S.C. §119 (e) of Provisional application 61/181,636, filed May 27, 2009, and provisional application 61/181,663, filed May 27, 2009, the entire contents of which are hereby incorporated by reference for all purposes as if fully set forth herein. This application is related to the following cases, the entire disclosures of which form a part of the present disclosure and are hereby incorporated by reference in their entirety for all purposes as if fully set forth herein: U.S. patent application Ser. No. 12/611,785 "Using Data Imputation To Determine And Rank Risks Of Health Outcome," U.S. patent application Ser. No. 12/476,907 "Individualized Ranking Of Risks Of Health Outcome," U.S. patent application Ser. No. 12/146,727, "Estimating Healthcare Outcomes For Individuals," U.S. Pat. No. 7,136,787, U.S. Patent Publication No. 20070038475, "Dynamic healthcare modeling," U.S. Patent Publication No. 20050288910, "Generation of continuous mathematical model for common features of a subject group," and U.S. Patent Publication No. 20050125158, "Generating a mathematical model for diabetes."

TECHNICAL FIELD

The present disclosure generally relates to computers configured to perform healthcare quality analysis. The disclosure relates more specifically to techniques useful in such computers for measuring the quality of healthcare.

BACKGROUND

Performance measurement in healthcare was introduced in response to evidence of wide variations in practices among physicians, inappropriate care, and high rates of people not receiving treatments known by professional organizations and guidelines to be effective. Since the performance measurement trend began, programs such as National Committee for Quality Assurance's (NCQA) Healthcare Effectiveness Data and Information Set (HEDIS) have stimulated increases in the use of evidence-based treatments. It is estimated that related improvements in performance are estimated to have prevented 1,900,000 heart attacks, 800,000 strokes, and 100,000 cases of end-stage renal disease in the first ten years of HEDIS.

However, the role of performance measurement is not limited to measuring quality. For example, performance measurement is increasingly used in "pay for performance" incentive programs for healthcare professionals. In such programs, the bonus earned by a physician may be partially or entirely based on metrics associated with a particular performance metric system.

Most methods of measuring performance are based on guidelines. For example, the HEDIS blood pressure measure, which counts the proportion of people with a diagnosis of hypertension who have systolic blood pressure (SBP) controlled to less than 140, is based directly on the seventh report of the joint national committee on prevention, detection, evaluation, and treatment of high blood pressure (JNC 7) guideline. When relying on guidelines such as the JNC 7 guideline, performance measures inherit the evidence that supports the guideline. This helps insure that improvements in performance on these measures will improve health outcomes. Furthermore, aligning performance measures to guidelines insures that physicians get consistent messages; they are not asked to do one thing by a guideline while their performance is measured against a different standard.

Guidelines focus on actions providers should take and how they should perform them. However, measures based on processes and treatment targets carry no information about the effects on health outcomes, do not permit comparisons of different measures, and provide no incentives to find the most effective and efficient ways to improve outcomes.

Performance measures based on guidelines also have the effect of turning guidelines into rules. Often, providers are penalized if they do not adhere to the measure, even in cases when the measure calls for an action that is inappropriate or unnecessary, and providers get no credit if go beyond the immediate target of a measure. Basing performance measures on particular guidelines tends to deemphasize other guidelines. There is no penalty if providers ignore guidelines for which there are no corresponding performance measures, and if the provider achieves the target of the measure he has delivered high quality care and can therefore cease care. Further, there is an incentive to preferentially allocate resources towards guidelines for which there are performance measures, and away from guidelines for which there are not.

Guidelines are issued in isolation of one another, since guidelines are designed by groups that have the greatest interest and expertise. As a result, there is no process for making comparisons across measures and no way to determine their relative importance. Further, giving each performance measure equal weight often leads to misplaced priorities. For example, one part of the third report of the expert panel on detection, evaluation, and treatment of high blood cholesterol in adults (Adult Treatment Panel III) recommendation, referred to herein as "ATP III" recommends controlling LDL cholesterol to below 100 mg/dL in people with cardiovascular disease (CVD), which reduces the patient's 30-year risk of a MI by about 39%. But controlling LDL cholesterol to below 160 mg/dL in people with fewer than two risk factors, as recommended by another part of the ATP III recommendation, reduces the patient's 30-year risk of a MI by about 5%. These two parts of the ATP III guideline not only have dramatically different impacts on the patient's risk, but they also have very different costs. Giving these two recommendations the same emphasis leads to inefficient use of resources and misplaced attention.

Most guidelines are clinically simplistic and tend to focus on one factor at a time, such as a patient's blood pressure. Guidelines also tend to use sharp cut-off points to separate those who should be treated from those who should not. An example of this is a hypertension guideline recommending that blood pressure be controlled to less than 140/90 mm Hg. These simplifications make guidelines easier for physicians to remember and patients to understand, but this simplicity can harm the quality and efficiency of care by encouraging the treatment of the wrong people.

Although performance measurement has undeniably improved the quality of care provided to patients, current methods of measuring performance do not go far enough.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

DETAILED DESCRIPTION

Figure 1:
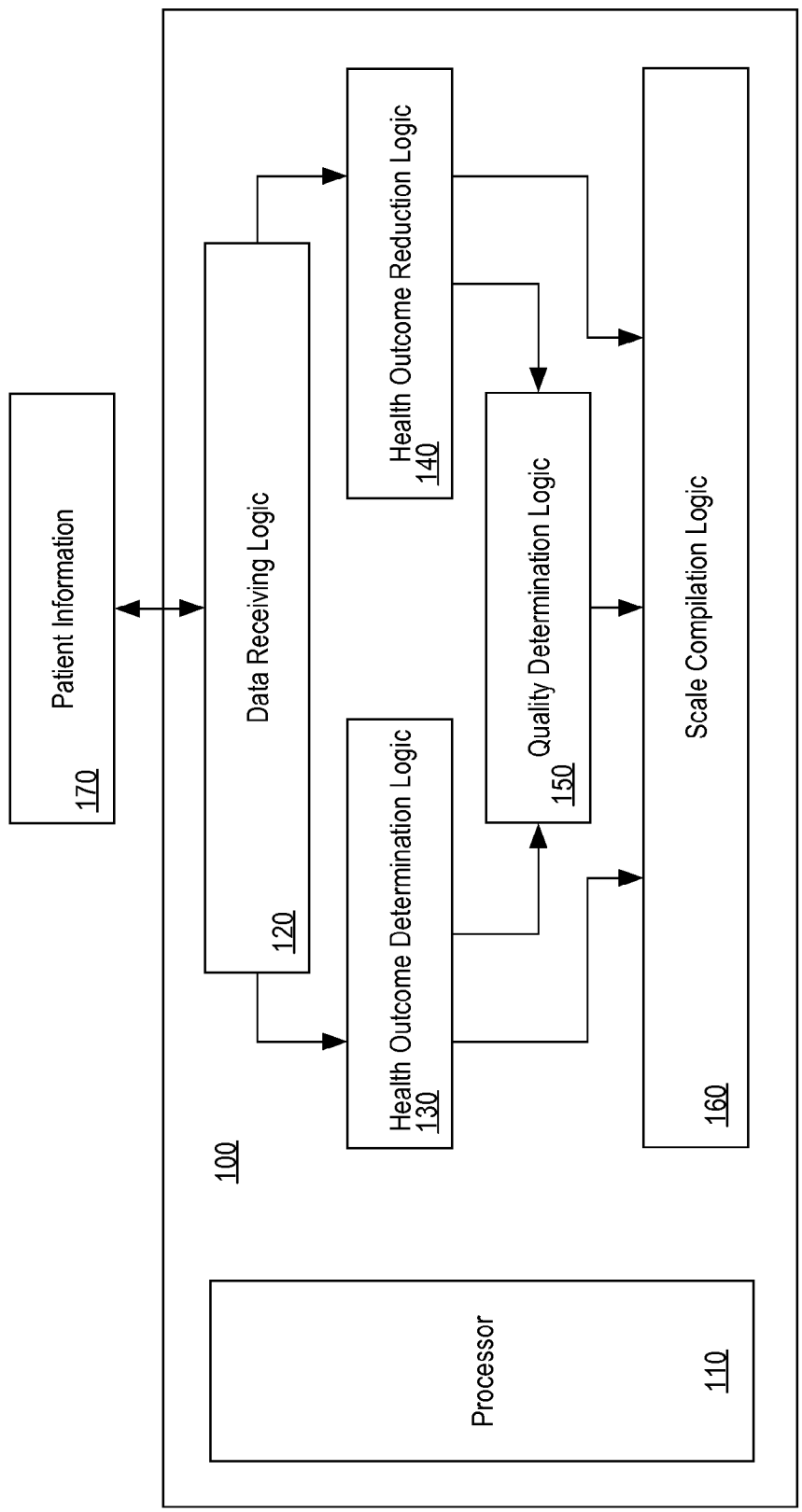
FIG. 1 illustrates an apparatus on which an embodiment may be implemented.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

A method of determining a quality of care provided by a healthcare provider to individuals in a population is disclosed.

In an embodiment, data representing a plurality of biomarkers for at least a portion of the individuals in a population is received. A baseline health outcome metric based on baseline treatment information associated with the population is determined. A current health outcome metric is determined based on current treatment information associated with the population. A current health outcome metric reduction value is determined as a difference between the baseline health outcome metric and the current health outcome metric.

In an embodiment, a health outcome metric is a quality of life metric that represents an adjusted quality of life value associated with the one or more healthcare outcomes, the baseline health outcome metric represents a baseline quality of life metric for the population, and the current health outcome metric represents a present quality of life metric for the population.

In an embodiment, a target health outcome metric representing a desired quality of life metric for the population and a potential health outcome metric reduction value as a difference between the baseline health outcome metric and the target health outcome metric are determined. The quality score value is based at least in part on the potential health outcome metric value. The target health outcome metric is assigned to the quality of care scale.

In an embodiment, a health outcome metric is a risk metric that represents the risk of the population incurring the one or more healthcare outcomes, the baseline health outcome metric represents a baseline risk of the population incurring one or more healthcare outcomes, and the current health outcome metric represents a present risk of the population incurring the one or more healthcare outcomes.

In an embodiment, a target health outcome metric representing a desired risk for the population incurring the one or more healthcare outcomes and a potential health outcome metric reduction value as a difference between the baseline health outcome metric and the target health outcome metric are determined. The quality score value based at least in part on the potential health outcome metric value and the target health outcome metric is assigned to the quality of care scale. In an embodiment, determining a quality score value comprises dividing the current health outcome metric by the potential health outcome metric.

In an embodiment, data representing a plurality of biomarkers for at least a portion of the individuals in a population is received. A baseline risk value representing a risk of the population incurring one or more healthcare outcomes is determined. A target risk value representing a desired risk for the population incurring the one or more healthcare outcomes is determined. Also, a current risk value representing a present risk of the population incurring the one or more healthcare outcomes is determined. A potential risk reduction value as a difference between the baseline risk value and the target risk value is determined. A current risk reduction value as a second difference between the baseline risk value and the current risk value is determined. A quality score value based at least in part on the current risk reduction value and the potential risk value is determined. The baseline risk and the target risk to a quality of care scale are assigned, and the quality score value is mapped to the quality of care scale.

In an embodiment, population data is received via the Archimedes Model. The Archimedes Model, commercially available through professional services from Archimedes, Inc., San Francisco, Calif., is a well-validated, realistic simulation of human physiology and disease and healthcare systems. These characteristics enable the Model to support research and decision-making about healthcare systems and policy at a level of detail previously not possible.

In one embodiment, determining a quality score value comprises dividing the current risk reduction value by the potential risk reduction value.

In another embodiment, assigning the baseline health outcome metric and the target health outcome metric to a quality of care scale comprises assigning the baseline health outcome metric to a low point of the quality of care scale and assigning the target health outcome metric to a high point of the quality of care scale.

In an embodiment, determining the baseline health outcome metric comprises determining an individual baseline health outcome metric of each of the individuals in the population, determining a sum of the individual baseline health outcome metric of all the individuals, and determining the baseline health outcome metric. In an embodiment, the baseline health outcome metric is determined per person year.

In an embodiment, the baseline health outcome metric comprises a risk that the population will incur the healthcare outcomes based on the population receiving none of one or more treatments that address the healthcare outcomes

Structural and Functional Overview

FIG. 1 represents a data processing apparatus 100 on which an embodiment may be implemented. The data processing apparatus 100 comprises a processor 110, which is coupled to data receiving logic 120, health outcome metric determination logic 130, health outcome metric reduction logic 140, quality determination logic 150, and scale compilation logic 160. Alternatively, the data processing apparatus 100 may comprise query receiving logic configured to receive queries for quality measurement information and query response logic configured to respond to queries for quality measurement information. A repository of patient information 170 is coupled to or accessible to the data receiving logic 120.

The data receiving logic 120 is coupled to health outcome metric determination logic 130 and health outcome metric reduction logic 140. Quality determination logic 150 is also coupled to health outcome metric determination logic 130 and health outcome metric reduction logic 140. Scale compilation logic 160 is coupled to health outcome metric determination logic 130, health outcome metric reduction logic 140, and quality determination logic 150.

In operation, patient information 170 is received by data receiving logic 120. Patient information 170 includes data representing a plurality of biomarkers for individuals in a population. The population may be based on a geographic region, based on the population of a healthcare provider, or any other population. Health outcome metric determination logic 130 is configured to determine a baseline risk metric representing a risk of the population incurring one or more healthcare outcomes or quality of life metric measuring the quality of life that a population can expect. For example, health outcome metric determination logic 130 may determine the risk of the population incurring a myocardial infarction (MI), or the number of quality-adjusted life-years that a population can expect (or other quality of life measurement). Health outcome metric determination logic 130 is further configured to determine a target risk value representing a desired risk for the population incurring the one or more healthcare outcomes or a target quality of life value representing a target number of quality adjusted life-years or other quality of life measurement. Health outcome metric determination logic 130 is also configured to determine the current risk value representing a present risk of the population incurring the one or more healthcare outcomes or the current quality of life value representing the current quality of life value expected.

In an embodiment, health outcome metric reduction logic 140 is configured to determine a potential risk reduction value as a difference between the baseline risk value and the target risk value. In an embodiment based on quality of life values, health outcome metric reduction logic determines a value that may be inversely proportional to the gain expected in quality-adjusted life-years. In other embodiments, the scale is altered so that a proportional metric may be used. Health outcome metric reduction logic 140 is further configured to determine a current risk reduction value as a second difference between the baseline risk value and the current risk value. In an embodiment, a current quality of life metric reduction value is determined instead of a current risk reduction value.

Quality determination logic 150 is configured to determine a quality score, based at least in part on the current risk reduction value and the potential risk value. In an embodiment, the score may be based only on the current risk reduction value. Scale compilation logic 160 is configured to assign the baseline risk and/or the target risk to a quality of care scale, and map the quality score to the quality of care scale.

In an embodiment, query response logic is configured to electronically a response that causes a computer to create a graphical representation based on the quality of care scale. The representation may include a graphical user interface. The graphical user interface may include controls, such as buttons, menus, drop-down lists, virtual knobs and dials, as well as text input fields and other interface controls. These interface controls allow users of the system to switch population profiles, generate new virtual population information, alter the baseline, target, and current values used to generate the display. All features discussed herein may be implemented as variables in the graphical user interface, and manipulated via controls.

The data processing apparatus 100 may be implemented in various embodiments using a single computer, multiple computers, one or more application-specific integrated circuits (ASICs) or other digital electronic logic, one or more computer programs, modules, objects, methods, or other software elements. For example, in one embodiment data processing apparatus 100 may comprise a special-purpose computer having particular logic configured to implement the elements and functions described herein. In another embodiment, data processing apparatus 100 may comprise a general purpose computer as in FIG. 8, loaded with one or more stored programs which transform the general purpose computer into a particular machine upon loading and execution.

In an embodiment, the arrangement of processor 110, data receiving logic 120, health outcome metric determination logic 130, health outcome metric reduction logic 140, quality determination logic 150, and scale compilation logic 160 improves the operation of a computer by permitting more efficient computation of a global quality score (GO Score) as separate logic is provided for receiving data, determining risk, determining a risk reduction, determining a quality value, and scaling the quality value. For example, pipelined operations may be used in this arrangement to handle masses of patient data. Further, some operational units may execute at different rates and the arrangement improves rapid and efficient computer operation, for example, by permitting data to be buffered at the receiving logic 120 while slower operations such as risk determination and quality determination proceed in separate logical units. The separation of scale compilation logic 160 enables the computer to adapt operations rapidly and efficiently so that different scaling logical units may be substitute to accomplish scaling to different alternative measures, as detailed below.

Embodiments also improve computer performance in other ways. For example, the arrangement of quality determination logic 150 compares the actual reduction in risk to the potential reduction in risk, and therefore the computer can adjust for factors such as age, race, and sex, that cannot be changed by the delivery system or community. In contrast, a computer of FIG. 1 can measure how well the delivery system or community accomplishes the goals that can be changed by the delivery system or community. Scale compilation logic 160 enables the computer to output a score signal or value that is normalized to other performance measures, and therefore providers can achieve a score of 100% on the scale if they achieve the goals of the old measurement system. Computer operation is further improved because the score normalization that is implemented in scale compilation logic 160 is not limited to use with any particular scale or guidelines. The score may be normalized to any set guidelines.

Global Quality Scoring

In an embodiment, global quality scoring uses person-specific information about the complete spectrum of risk factors and treatments in the population of interest to calculate the expected rates of the outcomes of interest over a specified time period, under three scenarios. The population could be a health plan's membership or the patients of a particular clinic or doctor, or a subpopulation representing a particular demographic (e.g., age, gender, ethnicity, or patients with a particular condition).

Figure 3:
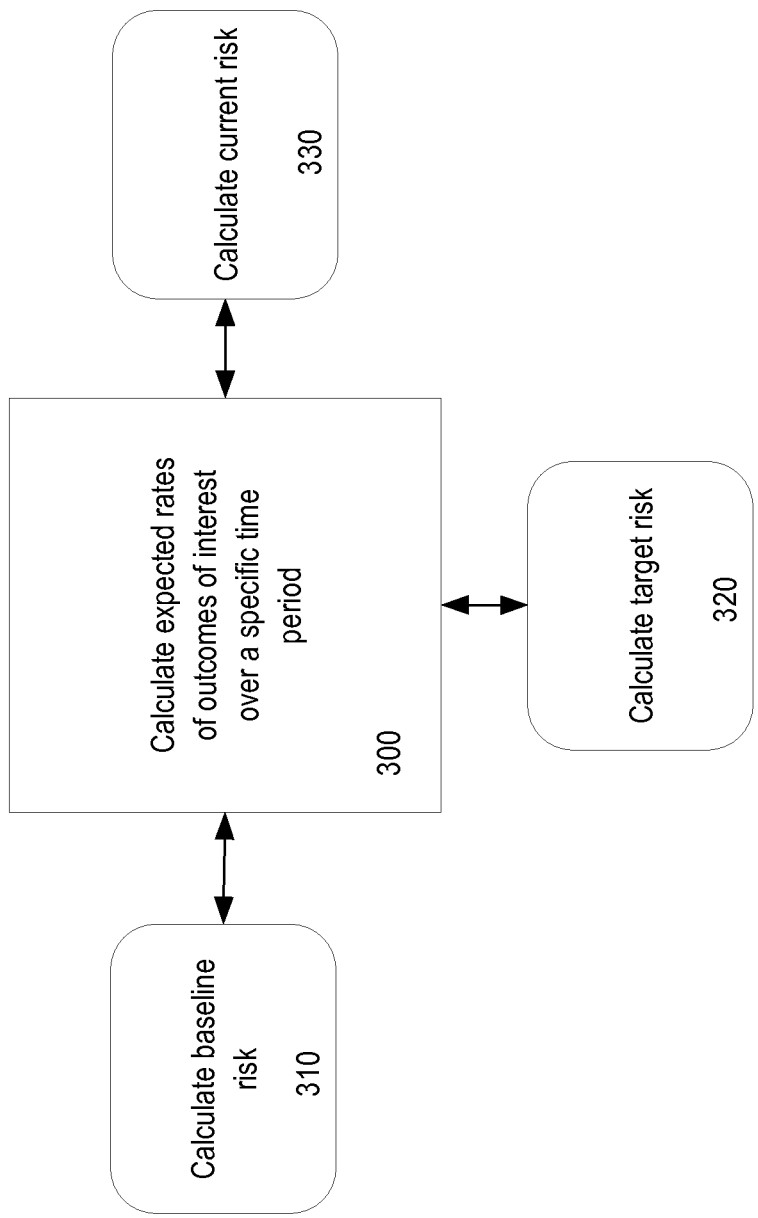
FIG. 3 is a flow diagram illustrating calculation of expected rates of health outcomes of interest.

FIG. 3 illustrates, in an embodiment, the determination of expected rates of health outcomes over a period of time at step 300. Three expected rates of outcomes of interest are calculated or determined in an embodiment. Each determination may be implemented in computer logic or computer program logic and may involve receiving data values representing real persons or virtual persons, transforming the data values according to the methods herein, and communicating the transformed data values over a network or storing the transformed data values.

A baseline health outcome metric such as risk is determined at step 310. In an embodiment, a baseline risk may represent the expected rate of an outcome of interest, such as a MI, if nobody in the population were taking treatment. A detailed discussion of an example baseline risk determination technique is described below with respect to FIG. 4.

A target health outcome metric such as risk is determined at step 320. In an embodiment, a target risk may represent the expected rate of outcome of interest assuming that every person is treated according to existing performance measures. A detailed discussion of an example target risk determination technique is described below with respect to FIG. 5.

A current health outcome metric such as risk is determined at step 330. In an embodiment, current risk represents the population's risk of the health outcomes of interest given the current levels of all risk factors. A detailed discussion of an example current risk determination technique is described below with respect to FIG. 6. The expected rates are used to create a scale and assign the current level of quality a score on that scale.

Any one or more of the above risk metrics may be optional in an embodiment. For example, a target risk may be optional in an embodiment that considers only the baseline risk and current risk.

In an embodiment, a baseline quality of life metric, current quality of life metric, and target quality of life metric may be calculated instead of risk-based metrics.

Baseline Risk or Quality of Life

Figure 4:
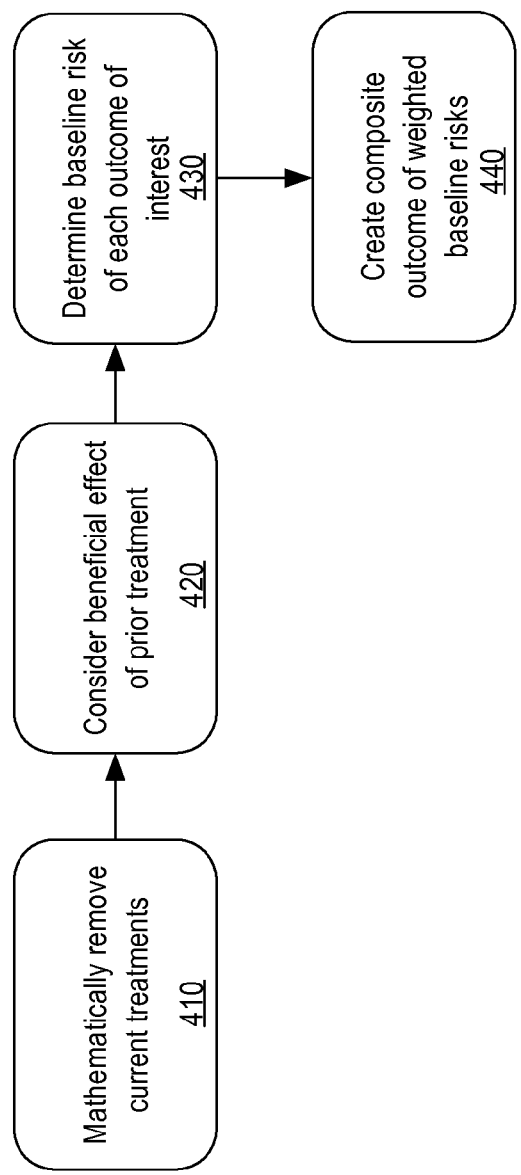
FIG. 4 is a flow diagram illustrating baseline risk determination.

FIG. 4 illustrates an example determination of a baseline health outcome metric such as baseline risk. In this context, baseline risk represents risks of the outcomes of interest if no one in the population is taking any treatments, and corresponds conceptually to a 0% physician performance level. However, people in the current population may already be participating in a beneficial treatment program. In an embodiment, to calculate the baseline risk, people in the population who are currently participating in a treatment program may be taken off their treatments mathematically, as in step 410.

Not all treatments or medical interventions need to be removed to generate a baseline. For example, the goal of the baseline in an embodiment may be to establish a point from which improvement is expected. That point may be based on time, events, or other factors. For example, a healthcare provider may wish to set the baseline based on the treatments that a patient was receiving at the time the patient joined the healthcare plan. The healthcare provider in this case may be less interested in the actual date that the patient joined the plan, and more interested in the treatments that the patient was taking at the time, or the prior "healthcare state" of the patient. Mathematically setting the baseline for that patient to his healthcare state at the time of joining the plan may involve mathematically removing additional treatments, and the effects of those treatments that were provided by the healthcare provider, but leaving the "old" treatments in place. If treatments were removed after the patient joined the plan, then those removed treatments would be mathematically added to generate the baseline. This allows the healthcare provider to generate a GO score that measures how much "better off" the patient is now than he would have been had he continued only the treatments offered by his previous provider.

This also allows a healthcare provider to measure the effectiveness of treatments initiated by or proprietary to the healthcare provider, such as smoking cessation programs and weight loss programs. Using the method described above, a patient may be taken off of an "old" weight loss program and placed on a "new" weight loss program by the provider. By setting the baseline to include the "old" program, the GO score will be based on the increase in effectiveness over the "old" weight loss program. Since weight loss and the way that weight loss is achieved affects many biomarkers besides weight, the GO score will provide credit for all improvements in health, and create accountability for negative impacts associated with unhealthy weight loss programs.

The method of step 410 can be illustrated with a simplified example using risk determinations from a risk modeling system. In one example, a person's current levels of risk factors give the person, who is already taking a thiazide, a five-year MI risk of 40%. In clinical trials thiazides reduce the MI risk by approximately 21%. Mathematically removing the current treatment in this case may involve performing determinations that remove any benefit derived from taking a thiazide, not just the benefit to a particular healthcare outcome; the patient is not actually instructed to cease taking medication for purposes of performing this determination. If this person were taken off of thiazides the risk of MI would increase to 40%/(100%−21%)=51%. The foregoing expression and multiple other similar expressions for other treatment programs and risk factors may be implemented in health outcome metric determination logic 130 or health outcome metric reduction logic 140, or represented in stored algorithms in a programmed computer system and applied to every person under consideration.

In one embodiment, the method takes into account other risk factors and treatments, and the benefit the patient had already obtained from past treatment as in step 420. For example, if an individual has had prior treatment that successfully reduced the degree of coronary artery plaque in the patient, the degree of coronary artery plaque expected given past history of risk factors and treatments may be taken into account in the configuration of the logic 130, 140 or in the stored algorithms. The baseline may be lowered based on this information, thereby adjusting the scale to reflect prior treatments.

In an embodiment, for each treatment a person is taking, a "baseline risk" of each outcome of interest is determined in step 430. For example, a first baseline risk may represent the risk of the patient having a MI, and a second baseline risk may represent the risk of the patient developing diabetes. If more than one outcome of interest exists, weights are assigned to the outcomes to create a composite outcome. In an embodiment, more than one composite outcome may be created in step 440. For example, the first (MI) baseline risk and the second (diabetes) risk may be combined to create a composite baseline risk. Each risk may be assigned a different weight value, which may be based on factors such as seriousness of the condition, rate of death associated with the condition, or any other factor. The baseline risks for the individual outcomes may be retained to understand the components of the composite outcome.

The baseline risks for each person are added and expressed as an appropriate rate in person-years to get the baseline risk for the population. The term "person-years" describes the length of time of experience or exposure of a group of people who have been observed for varying periods of time, and may be expressed as the sum total of the length of time each person has been exposed, observed, or at risk. The number of person years for expressing the rate of the outcome would be set to an appropriate magnification in order to make the score clinically meaningful. For example, 5-year MI rates may be expressed with a magnification of 1000 person-years. This value is assigned as 0 on the newly created quality scale.

In an embodiment, the baseline health outcome metric is based on quality of life, rather than risk. For example, the baseline quality of life metric may be determined based on quality-adjusted life-years. The metric may be inversely proportional to the number of expected life-years, so that a higher metric is associated with a positive outcome. Therefore, if a population is expected to have X number of quality adjusted life-years with no treatment plan, then the goal is to increase the number of life-years.

Target Risk or Quality of Life

Figure 5:
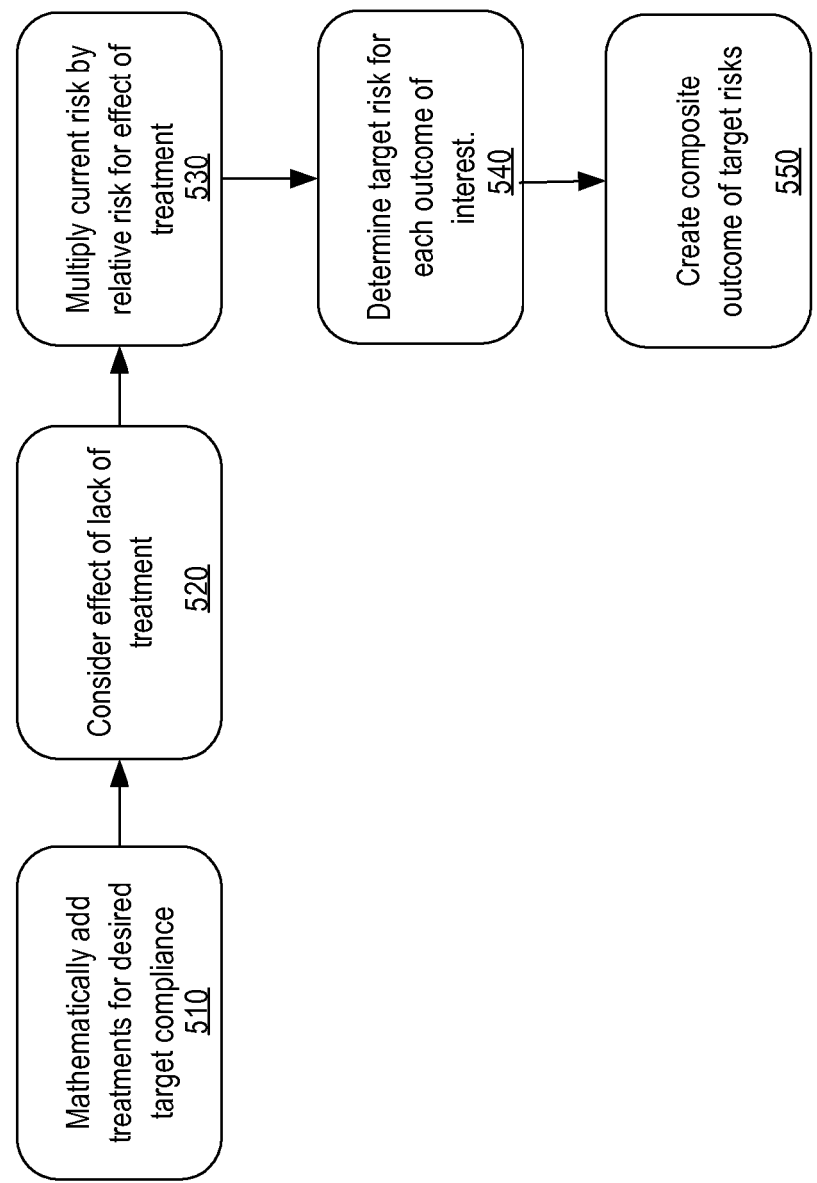
FIG. 5 is a flow diagram illustrating target risk determination.

FIG. 5 illustrates an example determination of a target health outcome metric such as target risk. Although target risk is the health outcome metric used in this example, target quality of life metric may be used instead. In this context, target risk represents a risk when it is assumed that every person is treated according to existing performance measures with 100% performance and compliance.

At step 510, each treatment desired for target compliance is considered as though each patient in the target population were participating in the treatment. For example if a person has hypertension and a SBP of 160, the risk would be calculated as if their blood pressure were decreased to the target of the performance measure.

As with the calculation of the baseline risk, at step 520 the method takes into account the patient's other risk factors, other treatments, and the chronic damage caused by living for years with untreated hypertension. For example, living for years with untreated hypertension may result in a greater level of coronary artery plaque, which would be taken into account in the calculation. The target risk may thus be lowered in an embodiment to provide a realistic scale that takes into account treatments that should have been adhered to by the patient, but were not adhered to.

In an embodiment, the target risk is determined at step 530 by multiplying the person's current risk by the relative risk for the effect of the treatment. For example, a relative risk value might be 0.79 for thiazides, since thiazides are known to reduce MI risk by approximately 21%. If a current risk for MI is determined to be 0.61, multiplying the current risk by the relative risk of 0.79 (taking into account the treatment involving thiazides) would yield a target risk value of about 0.48. At step 540, a target risk is optionally determined for each outcome of interest. For example, a target risk may be determined for another outcome, such as the development of diabetes. At step 550, a composite of target risks is optionally created. For example, a weighted score based on the MI target risk and the Diabetes target risk may be produced. The weights may be based on any factor, such as the likelihood of death resulting from each disease.

In an embodiment, the sum of each patient's target risks, when expressed per 1000 person years is the target risk for the population. This risk is assigned a value of 100% on the new quality scale.

Current Risk or Quality of Life

The current risk represents the population's risk of the health outcomes of interest given the current levels of all risk factors. It is calculated directly from the risk factors, without adding or subtracting any treatments.

Figure 6:
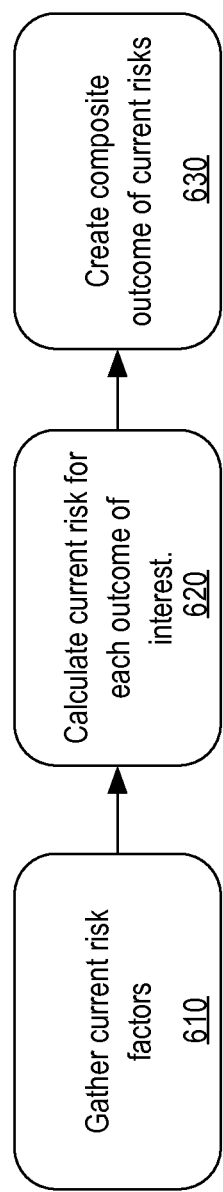
FIG. 6 is a flow diagram illustrating current risk determination.

FIG. 6 illustrates a current health outcome metric determination such as current risk determination in an embodiment. At step 610, current risk factors are gathered. For example, risk factors may include any behavior or historical attribute that may affect the health of the patient. Each risk factor may affect various outcomes of interest in a different way. Smoking, considered a risk factor in an embodiment, may affect the risk of having a MI differently than the risk of developing diabetes for example. At step 620, the current risk for each outcome of interest is calculated. The current risk may be determined using a healthcare modeling system, such as the Archimedes model. At step 630, a composite outcome of current risks is optionally created. For example, a weighted score based on the MI target risk and the Diabetes target risk may be produced.

In an embodiment, instead of current risk, current quality of life metric may be determined. Factors used to determine the current quality of life metric may include the current treatments that the population is participating in. Quality of life metrics may be determined through the use of a healthcare modeling system, such as the Archimedes model.

Global Quality Score (GO Score)

Figure 2:
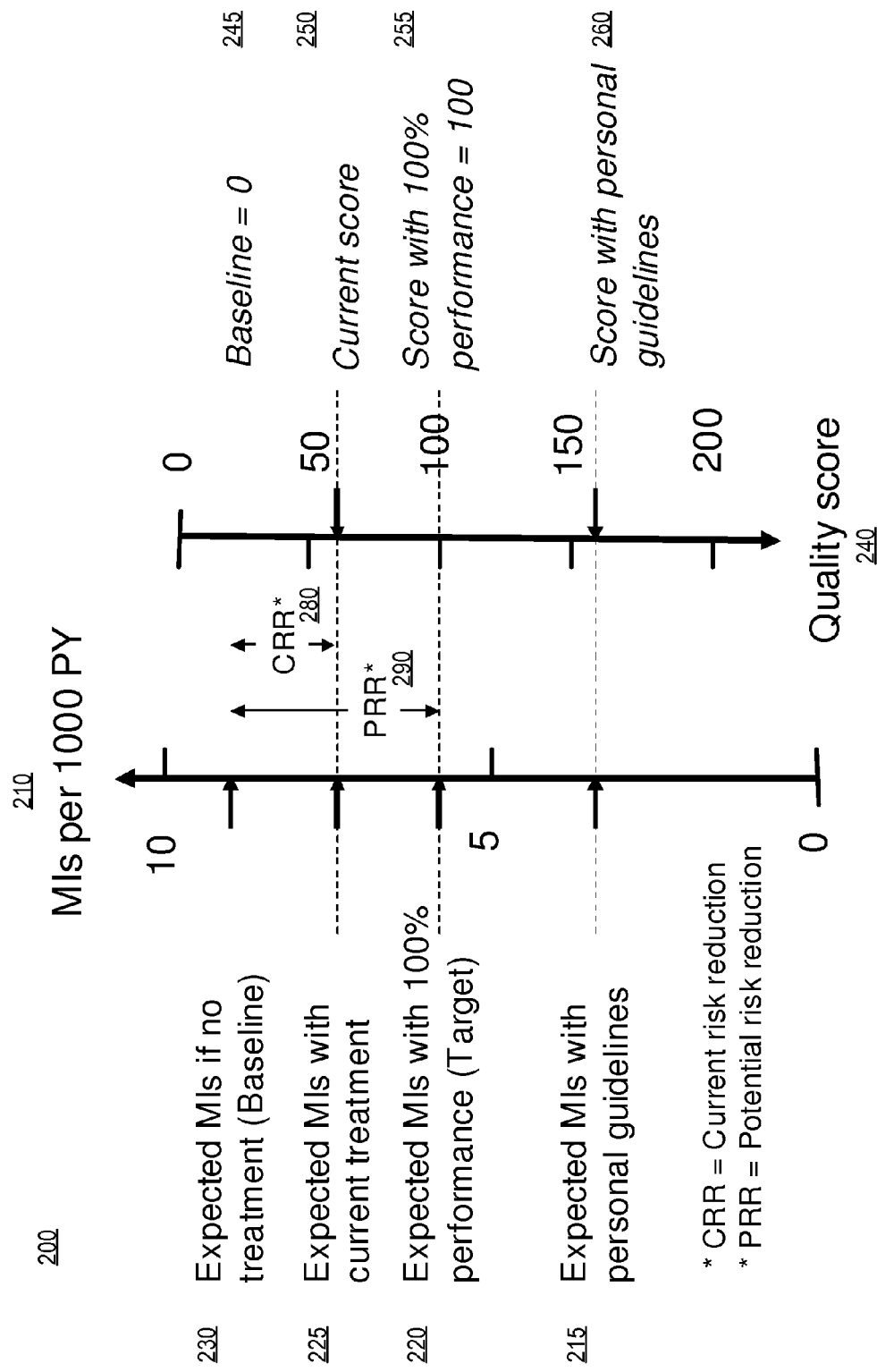
FIG. 2 illustrates a scale for representing an embodiment.
Figure 7:
FIG. 7 is a flow diagram illustrating global quality score (GO Score) determination.

FIG. 7 illustrates one example global quality score (GO Score) determination. A GO score set of proprietary methods and equations for predicting the risks, quality of life, life-adjusted years, and other factors an individual would have if their treatment were changed today, or that they would have had if their treatment history had been different. Once the baseline risk, target risk, and current risk have been determined, a global quality score for the population is calculated. FIG. 2 is a chart that represents the different risks as assigned to a quality scale. As discussed above, all metrics described herein may be based on health outcome metrics such as risk metrics and quality of life metrics. Although the embodiment discussed in FIG. 7 and other examples herein are directed to the use of risk-based metrics, quality of life-based metrics may be used instead.

At step 710, the difference between the baseline risk and the current risk is calculated, and is referred to herein as the "Current Risk Reduction". For example, the difference between the current score based on the expected number of MIs assuming current treatment continues and the score based on the baseline number of MIs (expected if there is no treatment) for a population is the current risk reduction.

At step 720, the difference between the population's baseline risk and target risk is calculated, and is referred to herein as the "Potential Risk Reduction". For example, the difference between the score based on the target number of MIs (expected with 100% compliance) and the score based on the baseline number of MIs (expected if there is no treatment) for a population is the potential risk reduction. This represents the maximum risk reduction that is possible with 100% intervention compliance.

The GO score is calculated based on the Current Risk Reduction and the Potential Risk Reduction. In an embodiment, at step 730, the GO score is calculated by dividing the Current Risk Reduction by the Potential Risk Reduction. The result represents the proportion of the potential risk reduction that providers have actually achieved. A detailed example of GO score calculation is found in the section below under the heading "Global Quality Score Illustration."

Because the GO score compares the actual reduction in risk to the potential reduction in risk, the GO score adjusts for factors such as age, race, and sex, that cannot be changed by the delivery system or community, and instead measures how well the delivery system or community accomplishes the goals that can be changed by the delivery system or community. For example, the delivery system or community can affect the quality of care that is actually delivered to a population.

The score a provider achieves is based on the risk of health outcomes, even though the GO score uses national guidelines for creating the scale. The score can exceed 100% if providers take actions that reduce risks more than the reductions achieved by just meeting current performance measures. This result occurs because the scale of the GO score has been generated to match the goals of the original performance scale. Thus, providers can achieve a score of 100% on the GO scale if they achieve the goals of the old measurement system. The actual score is not constrained by any particular set of guidelines or performance measures.

The GO score allows reduction in MIs and other health outcomes to be achieved using personal guidelines. Personal guidelines ensure that treatment is tailored to each person's specific risk profile. Traditional guidelines merely take a "one-size-fits-all" approach. The GO score may even be reported for sub-populations in addition to the overall population.

Although FIG. 2 discloses an embodiment wherein the GO score (quality score) is normalized to a particular set of guidelines, the GO score normalization technique described herein is not limited to use with any particular scale or guidelines. In addition, the GO score in this embodiment is based on risk. However, the GO score need not take risk into account. For example, the GO score may be based on quality of life metrics such as metrics that measure quality-adjusted life-years. The GO score may be normalized to any set guidelines, and may even be adjusted to fit multiple guidelines. For example, the GO score may be normalized to HEDIS guidelines, National Institute for Clinical Excellence (NICE) guidelines as published by the United Kingdom's technology assessment agency, and guidelines issued by France's Agence Nationale d'Accréditation et d'Evaluation en Santé (The National Agency for Accreditation and Health Care Evaluation), or ANAES.

The score may be reported for sub-populations as well as the overall population. All these can be calculated for the composite outcome as well as each component outcome. The scores can be calculated for any time horizon. Finally, scores can be repeated (e.g. annually) to monitor progress.

FIG. 2 shows a chart representing an example quality score scale 200. Scale 210 represents MIs per 1000 person years of a particular population. Scale 240 represents an embodiment of a global quality scoring scale 240 with the unit of measure being the global quality score.

Line 230 represents the number of MIs expected if no treatment were provided to the population. This includes the mathematical removal of current treatments. Line 230 is shared with line 245, which represents the baseline of the global quality scoring scale 240.

Line 225 represents the expected number of MIs that will occur if current treatment continues. Line 225 is shared with line 250, which represents the current score on the global quality scoring scale. Current risk reduction 280 represents the amount of risk currently being reduced by the treatments already underway.

Line 220 represents the number of MIs that would occur with 100% treatment according to current performance measures. Line 220 is shared with line 255, which represents a score of 100% on the new global quality scoring scale 240. Potential risk reduction 290 represents the total amount of risk reduction if current performance measures are met.

Line 215 represents the number of MIs expected if personalized guidelines are followed. Line 215 is shared with line 260, which represents the GO score expected if personalized guidelines are followed.

Adherence can be calculated from pharmacy data and used to scale the predicted risks. For example a patient whose adherence is 50% (picked up only 180 days of medications in the last year) could be assigned half the benefit (or more complex formulas for benefit as a function of adherence could be used if warranted.) Adherence from the past year may be used to forecast future adherence and hence future risk. Average risk from the previous year may also be used to scale the predicted risks. This may reduce the incentive for plans to lower risk just in time for evaluation.

Global Quality Score Illustration

The following examples illustrate the GO score and its benefits by calculating the GO score for one outcome, myocardial infarctions, and two treatments, cholesterol and hypertension management, in the Atherosclerotic Risk in Communities (ARIC) population over a five year period using a particular tool for calculating the effects of treatments.

ARIC is a prospective study conducted in four U.S. communities begun in 1987. In each community approximately 4,000 individuals aged 45-64 were randomly selected to participate, for a total of 15,792 participants.

From 1987 to 1989 each participant received an extensive initial examination, collecting medical, social, and demographic information. The participants were reexamined in 1990-92, 1993-95, and 1996-98, providing information about the occurrence of MIs as well as other outcomes. Because this study began 20 years ago, just as the first ATP guidelines were being introduced (1988) and five years before performance measures were introduced (1993), this population most closely represents the baseline risk. After removal of people already on treatment or contraindicated for treatment, 14,888 were eligible for treatment with either LDL cholesterol or blood pressure (BP) lowering drugs, or both. Follow-up data can be used to validate the calculation of baseline risk and to estimate the effect of different management strategies on MIs based on actual outcomes for this population.

For this illustration, GO scores that providers would have received are calculated with two different management strategies: (1) if the provider had achieved 80% performance on the LDL and BP measures; and (2) if the provider had been given flexibility to find more effective and efficient ways to reduce MIs.

In an embodiment, a programmed digital electronic computer may be programmed to be a "risk assessor" that calculates the GO score. In an embodiment, the computer uses a subset of available equations and is designed to enable rapid calculation of an individual's risk, and the effects of both stopping current treatments and starting new treatments. In another embodiment, all available risk equations are used.

In an embodiment, the risk assessor takes into account information on variables relating to demographics, behaviors, biomarkers, health history, and current medications. The variables may correspond to the same variables a physician would evaluate in the routine care of a patient. In one embodiment, the risk assessor can calculate the effects of at least the following treatments, given one-by-one or in any combination: statins, ACE inhibitors, beta blockers, thiazides, calcium channel blockers, aspirin, insulin, metformin, weight loss, and smoking cessation. It can calculate the following outcomes: MIs, strokes, onset of diabetes, diabetes complications (foot ulcers, blindness, ESRD), deaths attributable to any of these conditions, and costs. Additional risk factors, treatments, and outcomes can be added provided there is sufficient evidence and data.

Although a risk assessor is used in this illustration and has been described as having particular features, the value of the GO score and scale is independent of any particular risk calculation tool. Tools not conforming to the above description of a risk assessor could be used to gather information for calculating a GO score for a particular outcome provided it meets certain conditions. First, for whatever outcomes the tool is intended to calculate, it should include all populations of interest, all the pertinent risk factors, and all the interventions that modify them. Omission of a risk factor or treatment would have the effect of removing it from the options that providers should consider or would get credit for. Second, it should be able to calculate the effects of giving and removing treatments in a physiologically realistic way, such as taking into account the person's past history.

In an embodiment, the risk assessor calculates a baseline risk of MIs of 7.91 per 1000 person years for the ARIC population. This risk represents the zero line 245 on the scale 240 for the GO score. The risk assessor determines that if providers had achieved 100% performance on the current performance measures for cholesterol and blood pressure management in the ARIC population, the 5-year risk would have been 5.88. This risk represents the value of 100% on the new scale 240 at line 255. The Potential Risk Reduction is 7.91−5.88=2.03.

Additional metrics may be calculated on the assumption that providers had achieved a performance rate of 80% on both the LDL and blood pressure performance measures. Because the performance measures give equal credit for every patient who meets the target, for this illustration it is assumed that the 80% are a random sample of the people indicated for treatment by the current performance measures. On this assumption the risk assessor estimates that the risk would drop from a baseline risk of 7.91 to a "Current Risk" of 6.29. The "Current Risk Reduction" would then be 1.62, and the GO score would be 1.62/2.03=80%.

The GO score has the same value as the current performances measures (80%). This is because an 80% performance for the current level of care was specified, and it is in this sense the old and the new measures are comparable. However the GO score has several strengths compared to current performance measures.

First, the GO score carries information about the effects of improvements in performance on outcomes that are clinically meaningful. In this case, in the ARIC population, every point on the GO score represents about 2 MIs prevented per 1000 people per year. If a provider raises her performance to 85% on both measures she will know that she has prevented 2 MIs for every 1000 people in her panel.

Second, if providers were selective in whom they chose to treat or if there were a bias in the success rates of treating people with different levels of risk, those factors would be invisible to current performance measures but would show up in the GO score. For example, if the people who were being treated to the specified goal tended to come from lower risk people, which is likely because it is easier to achieve success with people who are closer to the goal to start, then the risk reduction calculated by the risk assessor would be lower than 1.62 and the GO score would be correspondingly lower; providers would be penalized for focusing on easy success. Conversely, if the bias was to successfully treat high risk people, an 80% performance on current measures would produce a GO score higher than 80%, and providers would receive credit for the extra effort.

Third, with the GO score, providers would get credit for treating patients even if their biomarkers did not reach the thresholds specified in current performance measures. For example providers would get credit if they lowered a patient's BP from 180 to 145.

Finally, providers would get credit if they treated people who would derive benefit, even if they are missed entirely by current performance measures, like the second patient in the earlier example using Table 1. Because the GO score is based on actual reductions in risk, it does not merely register whether some threshold is reached; it will give providers more credit if they lower the second patient's blood pressure from 138 to 120, than if they lowered the first patient's blood pressure from 142 to 138. The provider would get even more credit by lowering the second patient's LDL from 160 to 132, even though the current performance measure would give no credit for that.

In another illustration, the GO score is used to measure the quality of care given to a population and to compare two different treatment strategies of managing hypertension in the ARIC population. At the beginning of the ARIC project, there were approximately 2000 people in the ARIC population that were candidates for hypertension treatment according to the JNC 7 guidelines. These guidelines say people should be treated if BP<140/90 mmHg or if BP<130/80 mmHg if the patient has diabetes or chronic kidney disease.

For purposes of illustration, the population is randomly split into two groups, each having approximately 1000 people. The providers caring for both groups achieve 50% performance and compliance in treating their respective populations with hydrochlorothiazide (HTZ). This means that each group, 500 people are treated with HTZ. However, the providers use different methods of selecting the 500 people that are treated.

In group A, providers choose the 500 people at random. In group B, providers choose the people in order of risk of having an MI. In both cases, providers would have a 50% performance level on a scale such as the HEDIS hypertension scale. However, the two strategies would very different implications for actually preventing MIs. The GO score can be used to measure the disparity in the care provided to these two groups.

In this simplified example, using risk and population data as input and calculating the GO score for each population yields the results shown in Table 2. The potential risk reduction is 211−167=44. The actual risk reduction for group A is 211−189=22 and the GO score for group A is 22/44=50%. The actual risk reduction for group B is 211−178=33 and the GO score for group B is 33/44=75%.

TABLE 2

Rate of Myocardial Infarctions in the ARIC Population Elegible for Hypertension Treatment According to JNC 7 Guidelines Under Four Different Treatment Scenarios

| | Description | MI Rate per 100,000 Person Years | GO Score |
| --- | --- | --- | --- |
| Baseline | Nobody is treated | 211 | |
| Target | Everyone is treated | 167 | |
| Group A | 50% are treated, chosen at random | 189 | 50 |
| Group B | 50% are treated, chosen in order of risk | 178 | 75 |

This example illustrates several aspects of the GO score. In this embodiment, the GO score represents a measure of the quality of care based on health outcomes. Another aspect is that the GO score enables comparison between the quality of care delivered to two groups of people and allows measurement of the disparity of care between the two groups. This example also illustrates the ability of the score to measure differences in quality of care that are missed by traditional guidelines and performance measures.

The GO score may also be used to 1) determine the relative importance of different health factors; 2) compare the effects of different interventions to reduce disparities; and 3) design an optimal strategy for reducing disparities.

In an embodiment, a GO score may be based on life-years or quality-adjusted life-years rather than risk. This metric, other quality of life metrics and even risk-based metrics may be based on a hierarchy of inputs. For example, a GO score that measures the quality of care based on the number of quality adjusted life-years gained through treatment may only be indirectly tied to a particular disease. Treating one condition such as high blood pressure may also result in the treatment of another, such as high triglycerides. For example, exercise may result in a benefit associated with each of these conditions. The effect on each disease becomes a contributing factor to the GO score; by treating each disease, the quality adjusted life-years for each disease are counted toward the total, and a practitioner gets credit for the entire benefit derived from the treatment.

In an embodiment, calculating health outcome metrics may be performed for each treatment, for each individual. For example, the baseline health outcome metric may be determined by mathematically removing each treatment for each individual, with intermediate baseline metrics being determined. For example, calculating the baseline metric may consist of first determining a baseline date prior to the evaluation date and the patient's risk factors and treatments on or near the baseline date, then determining which changes in risk factors and treatments between the two dates can be attributed to the entity whose care performance is being scored, then predicting the risk factors and treatments the person would have on the evaluation date had they not benefited from the interventions and treatments provided by the entity, then calculating the predicted risks of the person on the evaluation date under this hypothetical scenario and comparing to the predicted risks of the person today based on their known risk factors and treatments in order to determine an attributable change in the composite health outcome metric (quality of life, life-years etc). The intermediate baseline metrics may be added to one another or combined in other ways to produce the overall baseline metric for a user, which may be combined with the baseline metrics for other users to generate an overall baseline metric. For each treatment removed for each patient, the effect on other health outcomes is considered.

The relationship between different changes in treatment and changes in risks may be quite complicated because the effect of treatments on risk can depend on many variables, because treatments may increase the risk of one outcome while reducing the risk of another, and because the effect of multiple treatments is not always a straightforward function of their individual impacts. For example, if a particular treatment that affects two health outcomes is removed, then the impact of the removal must be considered for each health outcome—for each individual. Applying a generalized gain or subtraction based on the removal (or even addition) of a treatment may result in an incorrect or skewed baseline calculation or potential calculation. For example, a particular patient may be taking two medications that, when taken alone, each provide a significant reduction of risk for myocardial infarction. However, the benefit may be an overlapping benefit such that each may reduce the risk of myocardial infarction by 25% when taken alone, but the combined benefit may result in a 30% risk reduction. If, for a population, the removal of the first medication were assumed to cause an increase of risk by 25%, the result would be incorrect. In fact, the removal of the first medication would only result in a 5% risk increase, and the subsequent removal of the second medication would result in a 25% increase. Therefore, when calculating baseline, target, and expected health outcome metrics, the addition or removal of treatments may be performed individually for each patient, for each treatment to ensure accuracy.

Additional Methods of Generating GO Scores

In an embodiment, a GO score is a ratio of two measures of reduction of risk. The numerator is a measure of the actual risk reduction due to treatment, and the denominator provides a benchmark that gives the score a more consistent meaning in the context of different plans and populations. The denominator may be set to a particular guideline, or standard derived from other data sources. A wide variety of numerators and denominators may be used in GO score generation.

For example, a benchmark (the denominator) may be based on data derived from the state of a population on a particular date, such as Jul. 4, 1990. The data from Jul. 4, 1990 would be gathered to build a model that includes factors such as age, gender, and other factors. Going forward in this example, measurements would be expressed in Jul. 4, 1990 health metric units. Expectations of risk may be derived from the model, and performance may be measured against the expectations derived from the model.

In an embodiment, a denominator used in a GO score generated as a ratio may provide a benchmark that provides a fair comparison between plans with healthy populations and plans or groups with older or unhealthy populations. It may also properly balance the incentive that plans might have to change their membership in order to get a high score so that the score does not encourage practices that run counter to the goal of providing improved care to the entire population. The denominator may be relatively stable over time in an embodiment. Different denominators may be used to serve different purposes.

For example, the denominator may represent a measure of risk reduction that is possible, or that is possible under certain cost-effectiveness constraints. A denominator may represent the risk reduction that is expected under some other measure, or may be based on data from current populations. A denominator could be specific to a particular region or demographic, depending on the relative difficulty of providing care to different regional or demographic groups.

The denominator could be a target treatment benefit based on the benefit that would be expected if certain guidelines were followed with 100% performance and compliance (this would normalize for the amount of treatment the population needs according to an independent method). As another example the denominator could be the expected total treatment benefit based on a model constructed from performance and compliance data for similar populations (this would normalize for the population's expected behaviors). As a third example the denominator could be the cost or estimated cost of the treatments (this would give a measure of the cost-effectiveness of the total treatment).

Example numerators include total untreated population risk, total possible risk reduction, total risk reduction attainable using certain cost-effectiveness thresholds, risk reduction associated with 100% compliance to published, standard or objective performance measures, expected risk reduction based on current care for the demographics of the population based on an empirical analysis of current risk reduction levels as a function of risk and demographic at some baseline point, and population size. Other numerators may also be used.

One consideration in choosing a denominator may be the population, or the total opportunity to treat. If the denominator includes a measure of the total opportunity to treat, it gives plans that have healthier populations the opportunity to get similar scores to those with unhealthy populations. Plans that have less healthy populations may be rewarded for taking on these patients and for the effort they expend to provide additional care for these patients. However, using population size in the denominator does not attempt to adjust for the fact that different populations may have different levels of treatable risk. For example, if the populations are very similar, using population size as a denominator would encourage plans to retain high risk members because it gives them more opportunities to increase their score.

The denominator may also be based on a measure of risk reduction. For example, the risk reduction may be based on current guidelines. This denominator may help normalize healthy vs. less healthy populations and may make the transition from current metrics easier. Guidelines, in this context, may include HEDIS guidelines or other standards.

Other considerations may include whether or not the denominator provides a smooth transition from other performance measures, or whether the denominator is likely to change over time as other outcomes are included in the metric and definitions of cost effectiveness change. For example adding measures of pain to the metric along with risk reduction, or changes in the quality of life assessments for different outcomes could change the denominators.

Other Risk Factors

The difference between current and untreated risk calculates risk reduction that is the result of medications. Risk is affected by many other factors however, some of which are incidental. For example a patient's family history could change because his brother has an MI. Others are biomarkers which can be modified through behavior or proper use of medication, such as A1c (a common blood test used to diagnose type 1 and type 2 diabetes), weight, blood pressure and lipids, or behaviors such as smoking.

In order to give physicians or plans credit for motivating positive behavior change it is important to capture risk changes over time that result from these efforts. These generally involve calculating "untreated risk" in the formulas using some or all of the patient's risk factors from some baseline time-point (e.g. the time they joined) possibly modified some expected aging change. If all risk factors are taken from the baseline time-point, then credit is given for all behavioral changes. On the other hand much of these changes is not the result of efforts by the plan, and could add statistical "noise" to the performance measure. The substitution could be made only for risk factors over which the plan has more influence on patient behavior (such as A1c) and could be further restricted to only those changes which exceed a certain threshold (e.g. only if weight loss exceeds 5%).

Additional Uses of GO Scoring

Creating a scoring system that is based on global quality allows for analyzing the savings generated by benefits achieved through performance. For example, if a reduction in MIs amounts to $35,000 in savings per MI avoided through treatment, the cost of the treatment may be compared with the savings generated by the treatment. As the level of performance increases, the cost of treatment will increase, and the savings will increase as the number of MIs approach zero.

Additionally, the GO score information may be used to prioritize treatments. For example, a guideline may suggest two different treatments for high blood pressure. Using the GO score, the actual benefit is used to measure performance, and the treatment with the greatest benefit may be given priority. Also, particular treatments may be prioritized for a group of patients, providing the treatment first to the patients deriving the greatest benefit from the treatment.

The GO score may be also weighted so that credit is given for reducing risk over time. Reducing a patient's risk with new treatment requires more effort and cost than maintaining a patient on current treatments. One way to give credit for this is to compare each patient treatments to those from some previous time-point (e.g. when the joined the plan or one year ago). Two risk reductions that may be calculated include the difference between current risk and untreated risk, and the difference between current risk and risk patient would have if on same treatment he had at the baseline point. The numerator could be constructed as a weighted sum of these two risk reductions—the weights dependent on the desired importance of these two contributions.

These two contributions may also be combined by determining typical rates at which patients stop treatments. An expected current risk may be calculated based on a fractional application of the baseline treatments where the fraction is the fraction of patients expected to be still on that treatment after the time elapsed since the baseline. This represents the current expected risk of the patient if the plan had not taken any special efforts to maintain the patient's treatment after they join. The difference of current risk and this expected risk provides a useful metric that rewards plans for both maintaining high levels of care and for increasing the level of care. This method can be combined with the first method described above, or other methods.

Regional Customization

If the patients in a particular geographic region or plan membership have higher or lower individual risks for certain outcomes than people with similar risk factors in other populations, then it is in the interests of optimal care for these additional risks to be calculated and incorporated in the treatment decision process. In an embodiment, customizations of the risk determinations for that population are provided, based on data for that population. Not basing the performance measure on risk determinations that are not customized may inhibit plans from using customized risks because their care may not be aligned with the performance measure. Thus, the performance metric may incorporate customized versions of the risk calculations to facilitate the alignment of care with performance measure.

Architecture

In one embodiment, apparatus 100 is implemented entirely on the same computer. In an embodiment, a multi-computer architecture may be used, but is not required. For example, software instructions for implementing the logical elements of FIG. 1 and patient information may be distributed using computer readable storage media such as a CD-ROM. A computer containing data receiving logic 120, health outcome metric determination logic 130, health outcome metric reduction logic 140, quality determination logic 150, and scale compilation logic 160, may use patient information 170 from a CD-ROM to generate and map the quality score value. In some embodiments, patient information 170 may be accessed over a network.

Alternatively, client/server architecture may be used. For example, one or more of the data receiving logic 120, health outcome metric determination logic 130, health outcome metric reduction logic 140, quality determination logic 150, and scale compilation logic 160 may exist on separate computers, connected via any communication medium. For example, the separate computers may be connected via the Internet, a dedicated network connection, or a proprietary network connection.

In one embodiment, the apparatus comprises a client computer that is coupled to and retrieves data from a central data source. Alternatively, the apparatus comprises a server, sending a response to a separate computer.

In another embodiment, a request may be sent from one computer and received by another computer which generates and returns a graphical representation using real-time information.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 8:
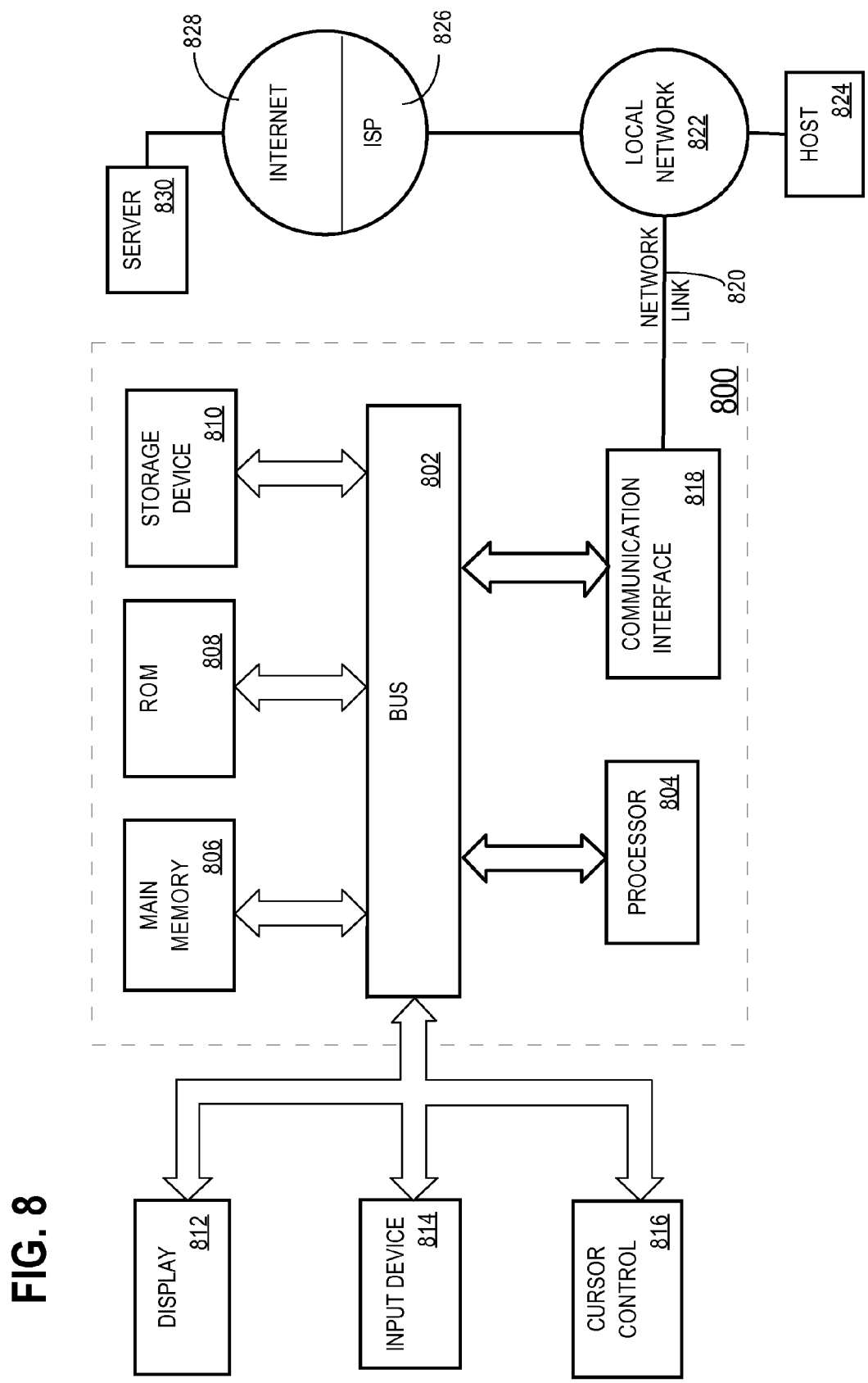
FIG. 8 illustrates a computer system upon which an embodiment may be implemented.

For example, FIG. 8 is a block diagram that illustrates a computer system 800 upon which an embodiment of the invention may be implemented. Computer system 800 includes a bus 802 or other communication mechanism for communicating information, and a hardware processor 804 coupled with bus 802 for processing information. Hardware processor 804 may be, for example, a general purpose microprocessor.

Computer system 800 also includes a main memory 806, such as a random access memory (RAM) or other dynamic storage device, coupled to bus 802 for storing information and instructions to be executed by processor 804. Main memory 806 also may be used for storing temporary variables or other intermediate information during execution of instructions to be executed by processor 804. Such instructions, when stored in storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk or optical disk, is provided and coupled to bus 802 for storing information and instructions.

Computer system 800 may be coupled via bus 802 to a display 812, such as a cathode ray tube (CRT), for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor 804 executing one or more sequences of one or more instructions contained in main memory 806. Such instructions may be read into main memory 806 from another storage medium, such as storage device 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 810. Volatile media includes dynamic memory, such as main memory 806. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on bus 802. Bus 802 carries the data to main memory 806, from which processor 804 retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818.

The received code may be executed by processor 804 as it is received, and/or stored in storage device 810, or other non-volatile storage for later execution.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

We claim:

1. A method for determining a quality of care provided by a healthcare provider to individuals in a population, comprising:
   receiving data representing a plurality of biomarkers for at least a portion of the individuals in the population;
   determining a baseline health outcome metric based on baseline treatment information associated with the population;
   wherein the baseline health outcome metric represents an expected rate of an outcome of interest obtainable if no person in the population had received a treatment;
   determining a current health outcome metric based on current treatment information associated with the population;
   determining a current health outcome metric reduction value as a difference between the baseline health outcome metric and the current health outcome metric;
   determining a quality score value based at least in part on the current health outcome metric reduction value;
   assigning the baseline health outcome metric to a quality of care scale;
   mapping the quality score value to the quality of care scale;
   determining a target health outcome metric representing a desired value of the metric for the population, wherein the target health outcome metric could be zero;
   determining a potential health outcome metric reduction value as a difference between the baseline health outcome metric and the target health outcome metric;
   determining the quality score value based at least in part on the potential health outcome metric value;
   assigning the target health outcome metric to the quality of care scale;
   wherein the steps are performed by one or more processors.

2. The method of claim 1, wherein determining a quality score value comprises dividing the current health outcome metric reduction value by the potential health outcome metric reduction value.

3. The method of claim 1, wherein the baseline health outcome metric represents a baseline risk of the population incurring one or more healthcare outcomes, and the current health outcome metric represents a present risk of the population incurring the one or more healthcare outcomes.

4. The method of claim 3, further comprising:
   determining the target health outcome metric representing a reduced risk for the population incurring the one or more healthcare outcomes;
   determining the potential health outcome metric reduction value as a difference between the baseline health outcome metric and the target health outcome metric;
   determining the quality score value based at least in part on the potential health outcome metric value;
   assigning the target health outcome metric to the quality of care scale.

5. The method of claim 4, wherein determining the quality score value comprises dividing the current health outcome metric reduction value by the potential health outcome metric reduction value.

6. The method of claim 4, further comprising determining a cost associated with the baseline risk, the current risk, and the target risk, wherein cost determination comprises subtracting a savings value associated with prevention of the one or more healthcare outcomes from a treatment cost associated with a risk level.

7. The method of claim 1, wherein determining the baseline health outcome metric comprises determining an individual baseline health outcome metric for each of the individuals in the population, determining a sum of the individual baseline health outcome metrics of all the individuals, and determining the baseline health outcome metric per person year.

8. The method of claim 1, wherein the baseline health outcome metric is based, at least in part, on one or more of:
   an assumption that the population is receiving or had received none of one or more treatments or medical interventions that address the healthcare outcomes;
   a prior healthcare state of the population; and
   deciding which changes in patient risk factors between two dates can be attributed to the efforts of the care provider or other entity whose efforts are being assigned a quality score.

9. The method of claim 1, further comprising mapping the quality of care scale to a performance scale that measures performance based on guidelines.

10. A non-transitory computer readable storage medium storing one or more sequences of instructions for determining a quality of care provided by a healthcare provider to individuals in a population, which instructions, when executed by one or more processors, cause the one or more processors to perform:
    receiving data representing a plurality of biomarkers for at least a portion of the individuals in the population;
    determining a baseline health outcome metric based on baseline treatment information associated with the population;
    wherein the baseline health outcome metric represents an expected rate of an outcome of interest obtainable if no person in the population had received a treatment;
    determining a current health outcome metric based on current treatment information associated with the population;
    determining a current health outcome metric reduction value as a difference between the baseline health outcome metric and the current health outcome metric;
    determining a quality score value based at least in part on the current health outcome metric reduction value;

assigning the baseline health outcome metric to a quality of care scale;

mapping the quality score value to the quality of care scale;

determining a target health outcome metric representing a desired value of the metric for the population, wherein the target health outcome metric could be zero;

determining a potential health outcome metric reduction value as a difference between the baseline health outcome metric and the target health outcome metric;

determining the quality score value based at least in part on the potential health outcome metric value;

assigning the target health outcome metric to the quality of care scale.

11. The non-transitory computer readable storage medium of claim 10, wherein the instructions that cause determining the quality score value further comprise instructions which, when executed, cause: dividing the current health outcome metric reduction value by the potential health outcome metric reduction value.

12. The non-transitory computer readable storage medium of claim 10, wherein the baseline health outcome metric represents a baseline risk of the population incurring one or more healthcare outcomes, and the current health outcome metric represents a present risk of the population incurring the one or more healthcare outcomes.

13. The non-transitory computer readable storage medium of claim 12, wherein the instructions further include instructions for:

determining the target health outcome metric representing a reduced risk for the population incurring the one or more healthcare outcomes;

determining the potential health outcome metric reduction value as a difference between the baseline health outcome metric and the target health outcome metric;

determining the quality score value based at least in part on the potential health outcome metric value;

assigning the target health outcome metric to the quality of care scale.

14. The non-transitory computer readable storage medium of claim 13, wherein the instructions that cause determining the quality score value further comprise instructions which, when executed, cause dividing the current health outcome metric reduction value by the potential health outcome metric reduction value.

15. The non-transitory computer readable storage medium of claim 13, further comprising instructions which, when executed by the one or more processors, cause the one or more processors to determine a cost associated with the baseline risk, the current risk, and the target risk, wherein cost determination comprises subtracting a savings value associated with prevention of the one or more healthcare outcomes from a treatment cost associated with a risk level.

16. The non-transitory computer readable storage medium of claim 10, wherein the instructions that cause determining the baseline health outcome metric further comprise instructions which, when executed, cause: determining an individual baseline health outcome metric for each of the individuals in the population, determining a sum of the individual baseline health outcome metrics of all the individuals, and determining the baseline health outcome metric per person year.

17. The non-transitory computer readable storage medium of claim 10, wherein the baseline health outcome metric is based at least in part on one or more of:

an assumption that the population is receiving none of one or more treatments or medical interventions that address the healthcare outcomes;

a prior healthcare state of the population; and deciding which changes in patient risk factors between two dates can be attributed to the efforts of the care provider or other entity whose efforts are being assigned a quality score.

18. The non-transitory computer readable storage medium of claim 10, further comprising instructions which, when executed by the one or more processors, cause the one or more processors to map the quality of care scale to a performance scale that measures performance based on guidelines.

19. An apparatus comprising:

one or more processors;

data receiving logic configured to receive data representing a plurality of biomarkers for at least a portion of individuals in a population;

health outcome metric determination logic configured to determine a baseline health outcome metric based on baseline treatment information associated with the population and a current health outcome metric based on current treatment information associated with the population; wherein the baseline health outcome metric represents an expected rate of an outcome of interest obtainable if no person in the population had received a treatment;

health outcome metric reduction logic configured to determine a current health outcome metric reduction value as a second difference between the baseline health outcome metric and the current health outcome metric;

quality determination logic configured to determine a quality score value based at least in part on the current health outcome reduction value;

scale compilation logic configured to assign the baseline risk to a quality of care scale and map the quality score value to the quality of care scale;

wherein the health outcome metric determination logic is further configured to determine: a target health outcome metric representing a desired value of the metric for the population; and a potential health outcome metric reduction value as a difference between the baseline health outcome metric and the target health outcome metric, wherein the target health outcome metric could be zero;

wherein the quality determination logic is further configured to determine the quality score value based at least in part on the potential health outcome metric value;

wherein the scale compilation logic is further configured to assign the target health outcome metric to the quality of care scale.

20. The apparatus of claim 19, wherein determining a quality score value comprises dividing the current health outcome metric reduction value by the potential health outcome metric reduction value.

21. The apparatus of claim 19, wherein the baseline health outcome metric represents a baseline risk of the population incurring one or more healthcare outcomes, and the current health outcome metric represents a present risk of the population incurring the one or more healthcare outcomes.

22. The apparatus of claim 21, wherein:

health outcome metric determination logic is further configured to determine: the target health outcome metric representing a reduced risk for the population incurring the one or more healthcare outcomes; and the potential health outcome metric reduction value as a difference between the baseline health outcome metric and the target health outcome metric;

quality determination logic is further configured to determine the quality score value based at least in part on the potential health outcome metric value;

scale compilation logic is further configured to assign the target health outcome metric to the quality of care scale.

23. The apparatus of claim 22, wherein determining the quality score value comprises dividing the current health outcome metric reduction value by the potential health outcome metric reduction value.

24. The apparatus of claim 22, wherein the scale compilation logic is further configured to determine a cost associated with the baseline risk, the current risk, and the target risk, wherein cost determination comprises subtracting a savings value associated with prevention of the one or more healthcare outcomes from a treatment cost associated with a risk level.

25. The apparatus of claim 19, wherein determining the baseline health outcome metric comprises determining an individual baseline health outcome metric for each of the individuals in the population, determining a sum of the individual baseline health outcome metrics of all the individuals, and determining the baseline health outcome metric per person year.

26. The apparatus of claim 19, wherein the baseline health outcome metric is based at least in part on one or more of:
- an assumption that the population is receiving none of one or more treatments or medical interventions that address the healthcare outcomes;
- a prior healthcare state of the population; and
- deciding which changes in patient risk factors between two dates can be attributed to the efforts of the care provider or other entity whose efforts are being assigned a quality score.

27. The apparatus of claim 19, wherein the scale compilation logic is further configured to map the quality of care scale to a performance scale that measures performance based on guidelines.

* * * * *